US00PP23178P3

(12) United States Plant Patent
Dirr

(10) Patent No.: US PP23,178 P3
(45) Date of Patent: Nov. 13, 2012

(54) ***LAGERSTROEMIA* PLANT NAMED 'PIILAG-III'**

(50) Latin Name: ***Lagerstroemia* L.**
Varietal Denomination: PIILAG-III

(75) Inventor: Michael A. Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 395 days.

(21) Appl. No.: 12/802,194

(22) Filed: Jun. 1, 2010

(65) Prior Publication Data

US 2011/0296572 P1 Dec. 1, 2011

(51) Int. Cl.
*A01H 5/00* (2006.01)

(52) U.S. Cl. ..... Plt./252

(58) Field of Classification Search ..... Plt./252
See application file for complete search history.

(56) References Cited

U.S. PATENT DOCUMENTS

PP16,917 P2 8/2006 Dirr

OTHER PUBLICATIONS

Plant Introductions, Inc.—page showing color pictures of *Lagerstroemia* selections, (including PIILAG-III) from booklet distributed at trade shows and to nurseries since Jan. 2010.

*Primary Examiner* — Wendy C Haas
(74) *Attorney, Agent, or Firm* — Greenlee Sullivan P.C.

(57) ABSTRACT

A new and distinct cultivar of *Lagerstroemia* plant named 'PIILAG-III', characterized by its compact, upright intermediate growth habit, red-purple new growth and dark green foliage in summer, red-purple fall color, true red flowers, and resistance to powdery mildew and *Cercospora* leaf spot.

4 Drawing Sheets

Genus and species of plant claimed: *Lagerstroemia* L.
Variety denomination: 'PIILAG-III'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'PIILAG-III'.

The new *Lagerstroemia* plant originated in 2006 from open-pollinated seed of 'Gamad I' (U.S. Plant Pat. No. 16,917). The cultivar 'PIILAG-III' originated and was discovered in a cultivated environment in Dearing, Ga.

Asexual reproduction of the new cultivar by stem cuttings in Watkinsville, Ga. since 2006 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG-III' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-III'. These characteristics in combination distinguish 'PIILAG-III' as a new and distinct cultivar: 1. Compact, upright, intermediate growth habit; 2. Red-purple new growth and dark green foliage in summer; 3. Red-purple fall color; 4. True red flowers; 5. Resistance to powdery mildew and *Cercospora* leaf spot.

Plants of the new *Lagerstroemia* 'PIILAG-III' differ from plants of the parent, 'Gamad I', primarily in flower color and growth habit. Plants of 'Gamad I' have cherry red flowers, and a low, spreading growth habit, whereas plants of 'PIILAG-III' have true red flowers and a more upright and overall larger growth habit.

BRIEF DESCRIPTION OF THE DRAWINGS

The accompanying color photographs illustrate the flower and foliage characteristics and the overall appearance of the new *Lagerstroemia*, showing the colors as true as it is reasonably possible to obtain in color reproductions of this type. Colors in the photographs may differ slightly from the color values cited in the detailed botanical description which accurately describe the colors of the new *Lagerstroemia.*

DETAILED DESCRIPTION

Figure 1:
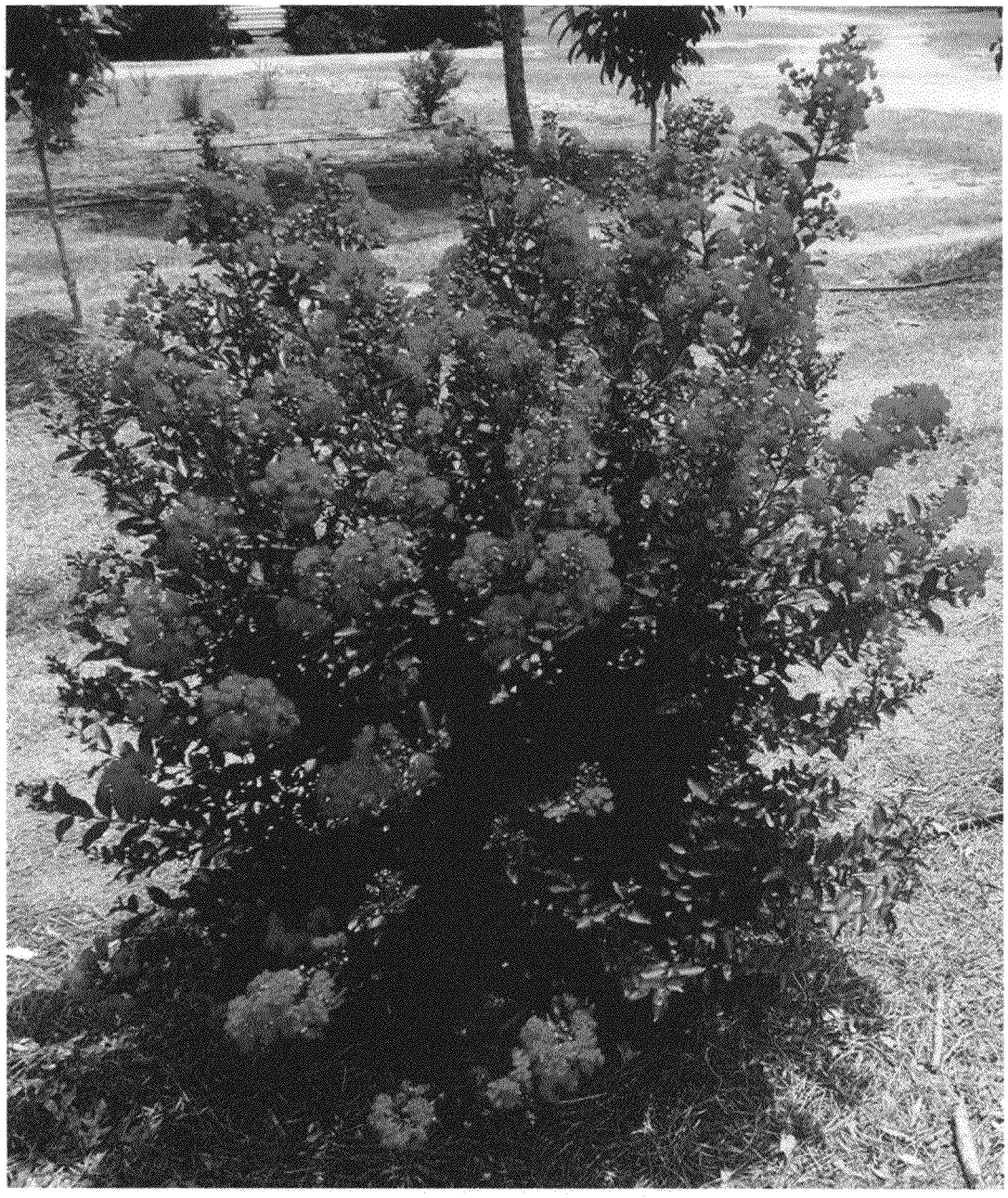
FIG. 1 illustrates the overall appearance of a mature plant of 'PIILAG-III'.
Figure 2:
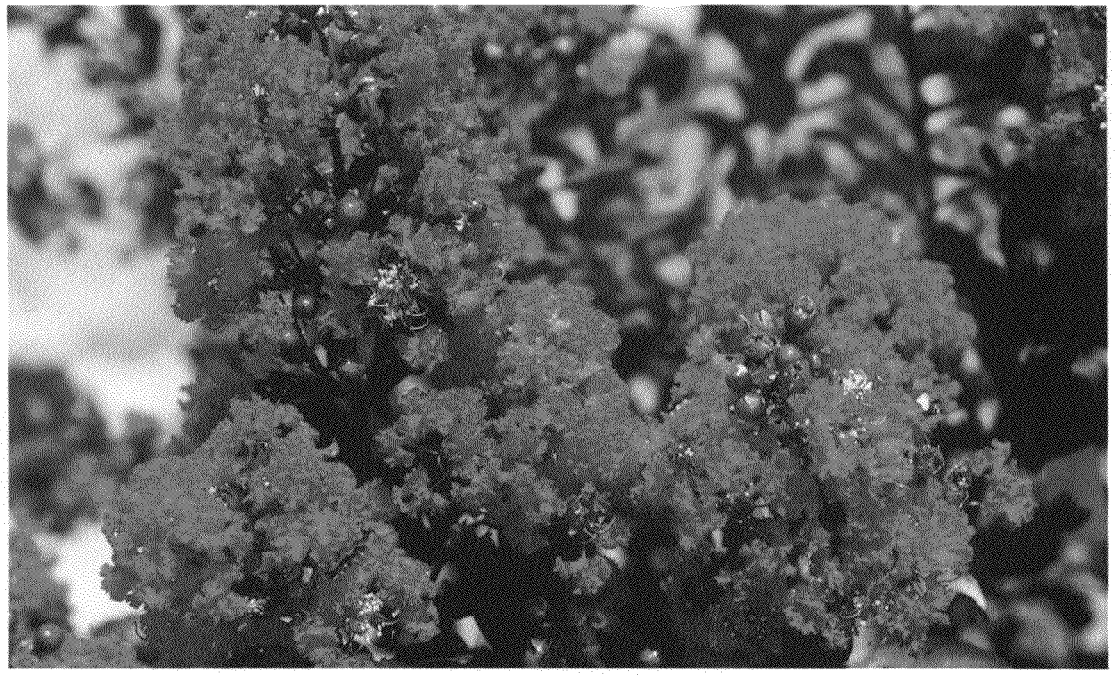
FIG. 2 illustrates a close-up view of the inflorescences of 'PIILAG-III'.
Figure 3:
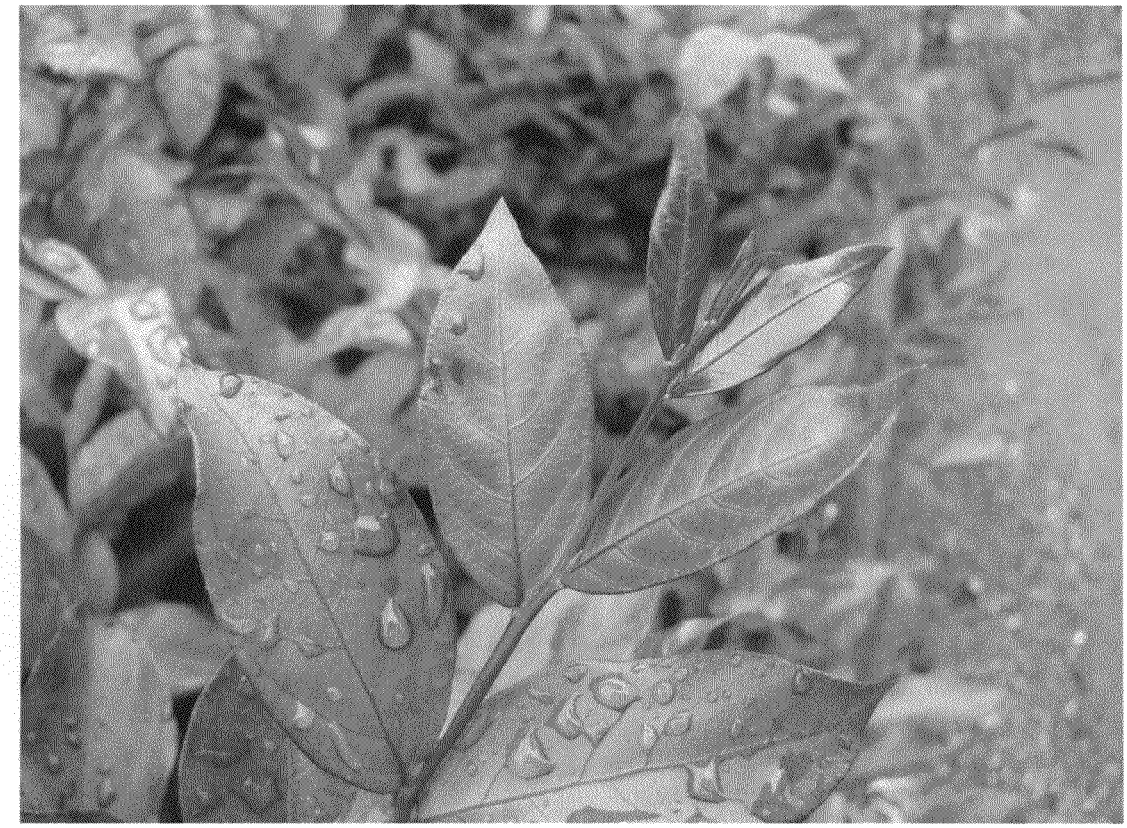
FIG. 3 illustrates a close-up view of the new growth of 'PIILAG-III'.
Figure 4:
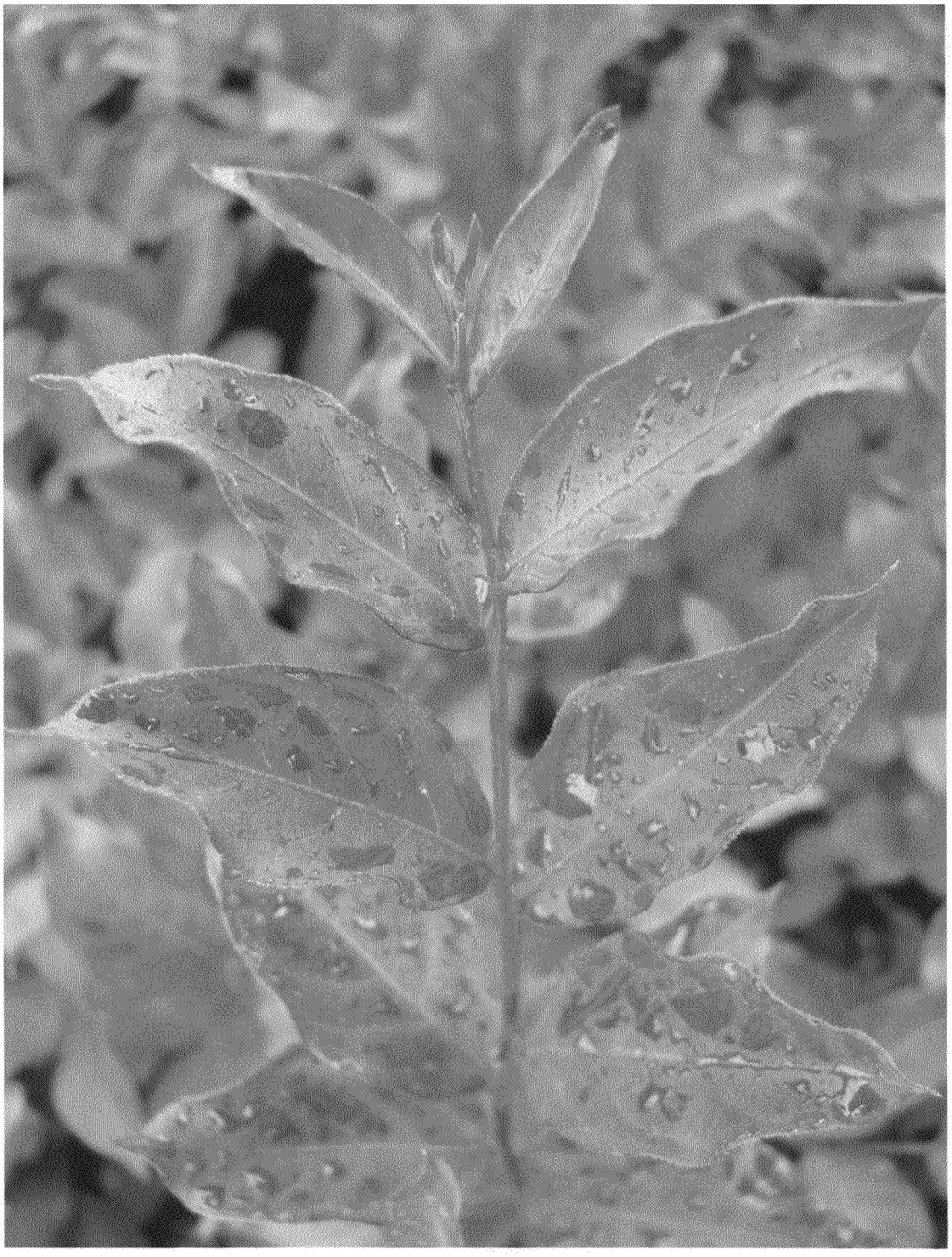
FIG. 4 illustrates a close-up view of the fall color of 'PIILAG-III'.

In the following description, color references are made to The Royal Horticultural Society Colour Chart, 2001 Edition, except where general terms of ordinary dictionary significance are used. Plants used for the description were approximately two and a half years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-III'.

Parentage:

*Female, or seed, parent.*—*Lagerstroemia* 'Gamad I'.

*Male, or pollen, parent.*—Unknown (open-pollinated).

Propagation:

*Type cutting*.—Terminal cuttings.

*Time to initiate roots, summer*.—About 21 days at 32 C. °.

Plant description: Flowering shrub; compact, upright growth habit. Freely branching; pruning enhances lateral branch development.

*Root description*.—Numerous, fine, fibrous and well-branched.

*Plant size*.—The original plant, now about four-years-old in the ground, is about 150 cm high from the soil level to the top of the inflorescences and about 120 cm wide.

*First year stems having a diameter of about* 2 *mm*.—Shape: squarish.

*Second year and older stems have a diameter of about* 5 *mm or more*.—Shape: round.

*Trunk diameter*.—About 2.2 cm at the soil line. Color: close to 199A.

*Internode length*.—About 1.5 cm.

*Strength*.—Flexible when young, easily broken once mature.

*First year stem color* (*young*).—Close to 180A. Color (woody): close to N199B.

*Second year and older stem color*.—Close to N199D.

*Bark*.—Exfoliates in strips beginning on second or third year stems.

Vegetative buds: Sub-opposite to alternate in arrangement, imbricate, conical, with no pubescence.

*Color*.—Close to 178B.

*Size*.—About 3 mm in length and 2 mm in width.

Foliage description:

*Arrangement*.—Sub-opposite to alternate, simple.

*Length*.—About 4.5 cm.

*Width*.—About 2.2 cm.

*Shape*.—Elliptical.

*Apex*.—Acuminate.

*Base*.—Cuneate.

*Margin*.—Entire.

*Texture* (*upper and lower surfaces*).—Glabrous.

*Venation pattern*.—Pinnate.

*Venation color of emerging foliage* (*upper and lower surfaces*).—181A.

*Venation color of fully expanded foliage* (*upper surface*).—Close to 146B.

*Venation color of fully expanded foliage* (*lower surface*).—Close to 146D.

*Color in developing foliage* (*upper and lower surfaces*).—Close to 183A.

*Color in fully expanded foliage* (*upper surface*).—Close to 147A.

*Color in fully expanded foliage* (*lower surface*).—Close to 147B. Some of the mature foliage is close to 187A.

*Color of leaf margin in developing foliage* (*upper and lower surfaces*).—181A. Color of leaf margin in fully expanded foliage (upper and lower surfaces) ranges from 181B to 146B.

*Fall color*.—Can be 179A, 183C, or any combination of these colors.

*Petiole length*.—About 2 mm.

*Petiole diameter*.—About 1 mm.

*Petiole color* (*upper and lower surfaces*).—Close to 146B.

*Pubescence*.—None.

Flower description: Flowers are produced from about June to September in Watkinsville, Ga. An inflorescence is showy for about two weeks, and individual flowers last about one day and are self-cleaning.

*Inflorescence type*.—Panicle.

*Inflorescence length*.—About 13 cm.

*Inflorescence width*.—About 10 cm.

*Peduncle*.—About 11.5 cm in length, about 2 mm in diameter, color is close to 183B, and no pubescence.

*Individual flowers*.—About 2.2 cm by 4 cm.

*Flower buds*.—Length: about 9 mm; Diameter: about 8 mm; Color: close to 187B, maturing close to 46A.

*Pedicels*.—About 1 cm in length, close to 53A in color, and no pubescence.

*Calyx*.—About 1 cm in length, about 8 mm in diameter, color close to 46A, and no pubescence.

Petals:

*Arrangement/appearance*.—Usually 6 per flower.

*Petal length*.—About 2 cm.

*Petal width*.—About 1.5 cm.

*Petal shape*.—Fan-shaped.

*Petal apex*.—Ruffled, rounded.

*Petal base*.—Sagittate.

*Petal margin*.—Ruffled.

*Petal texture* (*upper and lower surfaces*).—Glabrous.

*Petal color*.—Upper and lower surfaces are close to 53A.

Stamens:

*Quantity/arrangement*.—About 20 to 25 short stamens clustered in the center, about 8 mm long, filament color is close to 38B, and anther color is close to 14A. The short stamens are surrounded by 6 longer stamens, about 1.5 cm long. Filament color is close to 53A, and anther color is close to 14A. The stamens are not pubescent.

*Pollen*.—Produced in moderate quantities and is close to 9B in color.

Pistils:

*Quantity*.—One superior pistil per flower.

*Pubescence*.—None.

*Pistil length*.—About 2 cm in length.

*Stigma shape*.—Round, about 1 mm in diameter.

*Stigma color*.—Close to 148A.

*Style color*.—Close to 181A and about 1.3 cm in length.

*Ovary color*.—Close to 10B and about 3 mm in diameter.

Fruit:

*Type/appearance*.—Six-valved, dehiscent, broad ellipsoidal capsule.

*Length*.—About 9 mm.

*Diameter*.—About 8 mm.

*Mature color*.—Close to 200C. Each capsule contains many seeds that are about 6 mm long, 4 mm wide, and close to 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG-III', as illustrated and described herein.

* * * * *